US00PP18764P2

(12) United States Plant Patent
Hartman

(10) Patent No.: US PP18,764 P2
(45) Date of Patent: Apr. 29, 2008

(54) ***CALADIUM* PLANT NAMED 'MT. EVEREST'**

(50) Latin Name: *Caladium×hortulanum*
Varietal Denomination: Mt. Everest

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 11/648,871

(22) Filed: Dec. 29, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—C. A. Whealy

(57) ABSTRACT

A new and distinct cultivar of *Caladium* plant named 'Mt. Everest', characterized by its upright and outwardly arching plant habit; vigorous growth habit; undulate strap-like leaves; and green and white-colored leaves with red purple-colored venation.

3 Drawing Sheets

Botanical designation: *Caladium×hortulanum.*
Cultivar denomination: 'Mt. Everest'.

BACKGROUND OF THE INVENTION

The present invention relates to a new and distinct cultivar of *Caladium* plant, botanically known as *Caladium× hortulanum,* commercially referred to as a strap-leaf *Caladium* and hereinafter referred to by the name 'Mt. Everest'.

The new *Caladium* originated from a cross-pollination made by the Inventor in April, 2001, in Lake Placid, Fla. of the *Caladium×hortulanum* cultivar Grey Ghost, not patented, as the female, or seed, parent with the *Caladium× hortulanum* cultivar White Wing, not patented, as the male, or pollen, parent. The new *Caladium* was discovered and selected by the Inventor as a single plant within the progeny of the stated cross-pollination in a controlled environment in Lake Placid, Fla. on Jun. 15, 2002.

Asexual reproduction of the new cultivar by tuber divisions in a controlled environment in Lake Placid, Fla. since Apr. 15, 2003 has shown that the unique features of this new *Caladium* are stable and reproduced true to type in successive generations of asexual reproduction.

SUMMARY OF THE INVENTION

The cultivar Mt. Everest has not been observed under all possible environmental conditions. The phenotype may vary somewhat with variations in environment such as temperature and light intensity, without, however, any variance in genotype.

The following traits have been repeatedly observed and are determined to be the unique characteristics of 'Mt. Everest'. These characteristics in combination distinguish 'Mt. Everest' as a new and distinct cultivar of *Caladium:*

1. Upright and outwardly arching plant habit.
2. Vigorous growth habit.
3. Undulate strap-like leaves.
4. Green and white-colored leaves with red purple-colored venation.

In side-by-side comparisons conducted in Lake Placid, Fla., plants of the new *Caladium* differed from plants of the female parent, the cultivar Grey Ghost, in the following characteristics:

1. Plants of the new *Caladium* were shorter than plants of the cultivar Grey Ghost.
2. Leaves of plants of the new *Caladium* were strap-like whereas leaves of plants of the cultivar Grey Ghost were fancy types.
3. Leaves of plants of the new *Caladium* were more undulate than leaves of plants of the cultivar Grey Ghost.
4. Leaves of plants of the new *Caladium* were more rugose and more textured in appearance than leaves of plants of the cultivar Grey Ghost.
5. Plans of the new *Caladium* and the cultivar Grey Ghost differed in leaf coloration.

In side-by-side comparisons conducted in Lake Placid, Fla., plants of the new *Caladium* differed from plants of the male parent, the cultivar White Wing, in the following characteristics:

1. Under high light conditions, plants of the new *Caladium* were taller and more vigorous than plants of the cultivar White Wing.
2. Plants of the new *Caladium* and of the cultivar White Wing differed in leaf coloration as plants of the cultivar White Wing had creamy white and green leaves with pink to white-colored venation.

Plants of the new *Caladium* can also be compared to plants of the cultivar Gingerland, not patented. In side-by-side comparisons conducted in Lake Placid, Fla., plants of the new *Caladium* differed from plants of the cultivar Gingerland in the following characteristics:

1. Plants of the new *Caladium* were taller than plants of the cultivar Gingerland.
2. Plants of the new *Caladium* and the cultivar Gingerland differed in leaf coloration as plants of the cultivar Gingerland had red-spotted leaves with white-colored venation.
3. Plants of the *Caladium* had longer leaf petioles than plants of the cultivar Gingerland.

BRIEF DESCRIPTION OF THE PHOTOGRAPHS

The accompanying photographs illustrate the overall appearance of the new *Caladium.* These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet comprises a side perspective view of a typical plant of 'Mt. Everest' grown in a container.

The photograph on the second sheet comprises a side perspective view of typical plants of 'Mt. Everest' grown in a ground beds in an outdoor nursery.

The photograph at the top of the third sheet is a close-up view of typical inflorescences of 'Mt. Everest'.

The photograph at the bottom of the third sheet is a close-up view of typical tubers of 'Mt. Everest'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in 15-cm containers in Lake Placid, Fla., during the spring in a polyethylene-covered shadehouse and under conditions and practices which approximate those generally used in commercial *Caladium* production. During the production of the plants, day temperatures ranged from about 21° C. to 38° C., night temperatures ranged from about 10° C. to 21° C. and light levels about 8,000 foot-candles. Plants were about seven weeks from planting tubers when the photographs and the detailed description were taken.

Botanical classification: *Caladium×hortulanum* cultivar Mt. Everest.

Parentage:

*Female, or seed, parent.*—*Caladium×hortulanum* cultivar Grey Ghost, not patented.

*Male, or pollen, parent.*—*Caladium×hortulanum* cultivar White Wing, not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description.*—Number of buds per tuber: About five actively growing buds/shoots and about 18 dormant buds. Height: About 2.8 cm. Diameter: About 5.8 cm. Texture: Thick, starchy; somewhat brittle. Color: Epidermis, 200A with areas of 200D; interior, 6D. Root description/habit: Dense, thick and white fleshy roots with finer lateral roots.

Plant description:

*Plant/growth habit.*—Upright and outwardly arching plant habit. Vigorous growth habit; suitable for 10-cm to 25-cm containers. Mostly upright leaf petioles.

*Plant height, from soil level to top of leaf plant.*—About 20 cm.

*Plant height, from soil level to top of inflorescences.*—About 40 cm.

*Plant spread.*—About 33 cm.

*Cataphylls.*—Length: About 7 cm. Width: About 1.6 cm. Shape: Linear to elliptic. Apex: Acuminate. Base: Sheathing the stem. Color, outer surface: Lighter than 177D; streaks, N186A. Color, inner surface: Lighter than 170D; streaks, N186A.

Foliage description:

*Length.*—About 16.5 cm.

*Width.*—About 10.4 cm.

*Shape.*—Ovate to lanceolate.

*Apex.*—Acuminate.

*Base.*—Sagittate to peltate.

*Margin.*—Entire; undulate.

*Texture, upper surface.*—Smooth, glabrous; rugose giving a textured appearance.

*Texture, lower surface.*—Smooth, glabrous; glaucous; rugose giving a textured appearance.

*Venation pattern.*—Pinnate.

*Color.*—Developing leaves, upper surface: Margins: Darker than 137A. Center: Intervenal areas, 145D and 194D, suffused with 137A. Venation: 59A to 59B. Developing leaves, lower surface: Margins: 191A to 191B. Center: Intervenal areas, 191A to 191B. Venation: Laterals and midvein, 147D tinged with 182D; areas surrounding veins, 145D. Fully developed leaves, upper surface: Margins: Darker than 137A. Center: Intervenal areas, 194D, suffused with 137A. Venation: 59A to 59B; areas surrounding veins, 155C. Fully developed leaves, lower surface: Margins: 191A. Center: Intervenal areas, 191A. Venation: Laterals and midvein, 147C to 147D tinged with 182D; areas surrounding veins, 155C.

*Petiole.*—Aspect: Mostly erect, outwardly arching with development. Length: About 18 cm. Diameter, distal: About 3.6 mm. Diameter, proximal: About 7 mm. Strength: Strong; flexible. Color: 148B to 148C; bars and streaks, 186A to 186B. Wing length: About 4.9 cm. Wing diameter: About 6 mm. Wing color, outer and inner surfaces: 148B; streaks, N186A.

Inflorescence description:

*Inflorescence arrangement.*—Hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers developed between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about twelve weeks after growth commences. Inflorescences last about three days before fading; inflorescences persistent.

*Spathe.*—Length: About 15.3 cm. Width: About 4.3 cm. Shape: Ovate to elliptic. Apex: Acuminate. Base: Tapering. Margin: Entire. Texture, upper and lower surfaces: Smooth, glabrous. Color: When developing, front surface: Upper two-thirds: 147D tinged with 158D. Lower one-third: 147C Flushed with 187A. When developing, rear surface: Upper two-thirds: 146C to 147C tinged with 158C. Lower one-third: 147B. Fully developed, front surface: Upper two-thirds: 158D tinged with 50D; with development, 199D tinged with 145B. Lower one-third: 147C flushed with 187A; with development, 147B. Fully opened, rear surface: Upper two-thirds: 158Flushed with 36B; central rib, tinged with 146C. Lower one-third: 147B.

*Spadix.*—Length, entire spadix: About 8.6 cm. Length, male flower zone: About 5.3 cm. Length, sterile flower zone: About 1.3 cm. Length, female flower zone: About 2 cm. Diameter, male flower zone: About 1.2 cm. Diameter, sterile flower zone: About 9.5 mm. Diameter, female flower zone: About 1.1 cm. Shape: Columnar. Apex: Obtuse. Base: Obtuse. Aspect: Upright. Color: Immature, male zone: 158D. Immature, female zone: 24D. Mature, male zone: 11C. Mature, female zone: 25D.

*Female flowers.*—Quantity per spadix: About 135. Shape: Ovate to elliptic. Height: About 3 mm. Diameter: About 3 mm. Stigma color: 27C. Ovary color: 25D.

*Male flowers.*—Quantity per spadix: About 150. Shape: Obovate; inverted triangle. Height: About 4 mm. Diameter: About 4 mm. Anther color: 11C. Amount of pollen: Abundant. Pollen color: 8C.

*Space.*—Length: About 33 cm. Diameter: About 7 mm. Strength: Sturdy; flexible. Aspect: Erect. Texture: Smooth, glabrous; glaucous. Color: Towards the apex, 147B to 146A, streaks, N186A; towards the base, 146A to 197D, streaks, N186A.

*Seed and fruit.*—Seed and fruit development has not been observed on plants of the new *Caladium.*

Disease/pest resistance: Plants of the new *Caladium* have not been observed to be resistant to pathogens or pests common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'Mt. Everest' as illustrated and described.

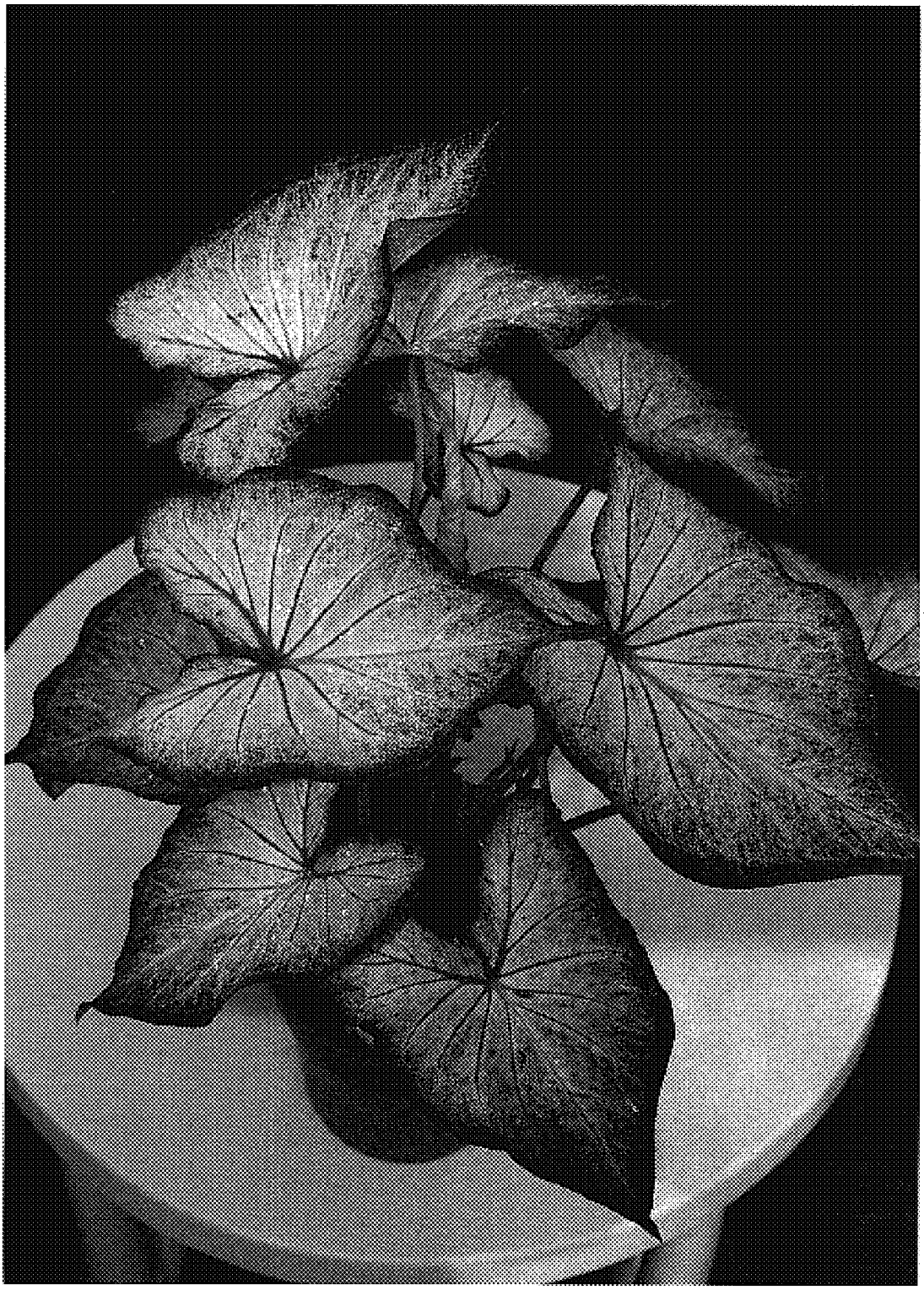

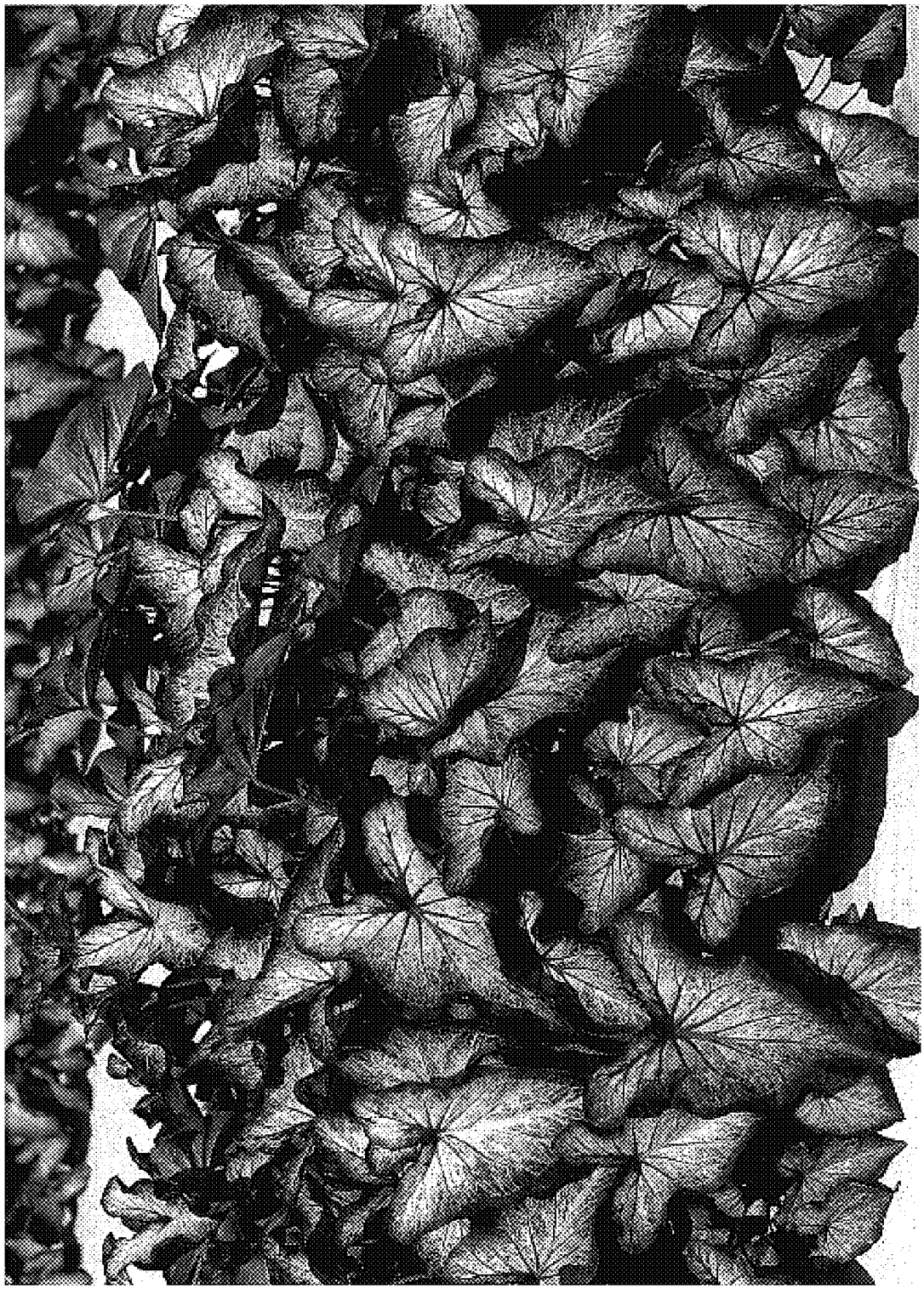

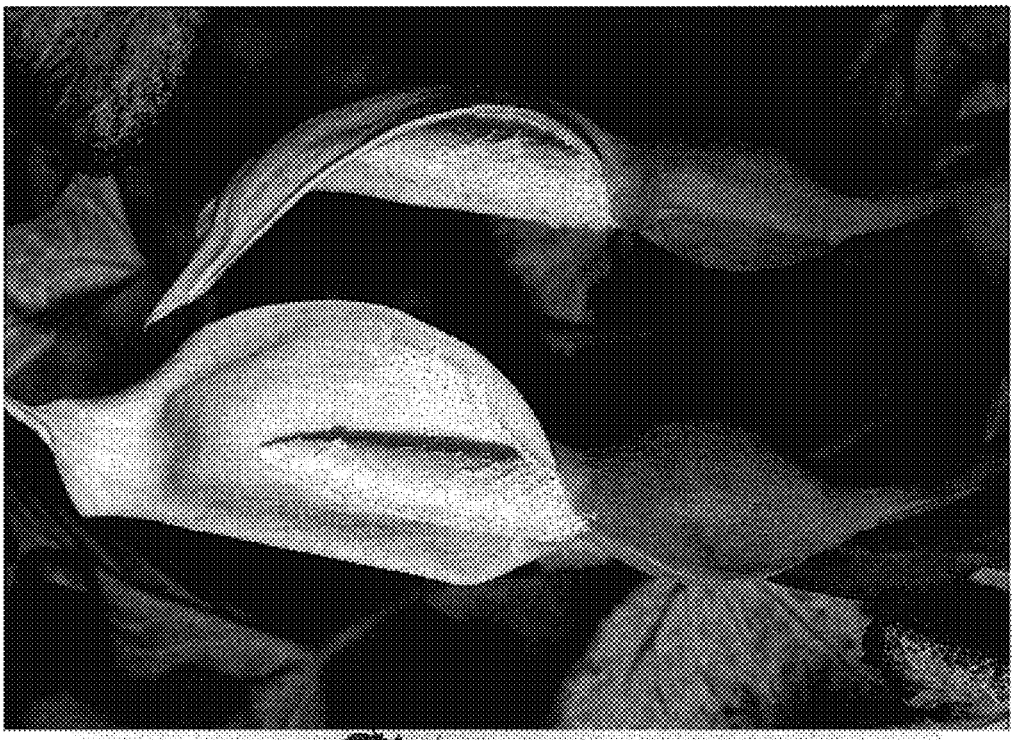
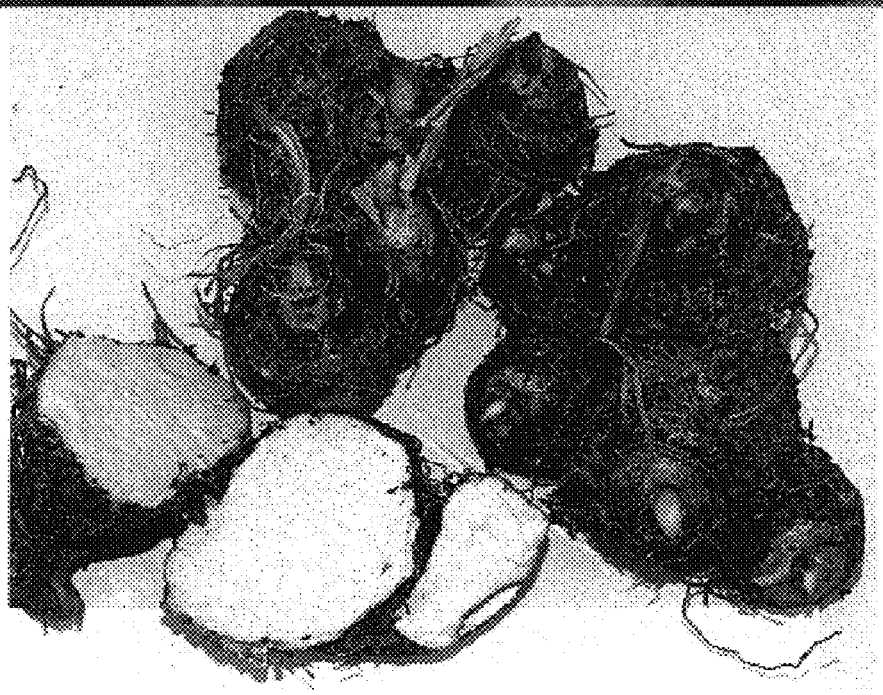

* * * * *